(12) United States Patent
Dinarello

(10) Patent No.: US 10,548,870 B2
(45) Date of Patent: Feb. 4, 2020

(54) METHOD FOR TREATING MULTIPLE SCLEROSIS

(71) Applicant: OLATEC THERAPEUTICS LLC, New York, NY (US)

(72) Inventor: Charles A. Dinarello, Boulder, CO (US)

(73) Assignee: OLATEC THERAPEUTICS LLC, New York, NY (US)

( * ) Notice: Subject to any disclaimer, the term of this patent is extended or adjusted under 35 U.S.C. 154(b) by 0 days.

(21) Appl. No.: 16/458,595

(22) Filed: Jul. 1, 2019

(65) Prior Publication Data

US 2019/0321325 A1 Oct. 24, 2019

Related U.S. Application Data

(63) Continuation-in-part of application No. PCT/US2018/012455, filed on Jan. 5, 2018.

(60) Provisional application No. 62/443,171, filed on Jan. 6, 2017.

(51) Int. Cl.
*A61K 31/275* (2006.01)
*A61P 21/00* (2006.01)
*A61K 9/00* (2006.01)

(52) U.S. Cl.
CPC .......... *A61K 31/275* (2013.01); *A61K 9/0053* (2013.01); *A61P 21/00* (2018.01)

(58) Field of Classification Search
CPC ...... A61K 31/275; A61K 9/0053; A61P 21/00
USPC ........................................................ 514/665
See application file for complete search history.

(56) References Cited

U.S. PATENT DOCUMENTS

| 9,278,082 B2 * | 3/2016 | St Laurent ............... A61K 9/06 |
| 9,439,880 B2 * | 9/2016 | St Laurent ........... A61K 9/0014 |
| 2012/0177632 A1 | 7/2012 | Shinohara et al. |
| 2016/0256430 A1 | 9/2016 | St. Laurent |

FOREIGN PATENT DOCUMENTS

WO 2017184735 A1 10/2017

OTHER PUBLICATIONS

Coll et al., Nature Medicine, 2015, 21(3) 248-257 (Year: 2015).*
Shao et al "NLRP3 inflammasome and its inhibitors: a review" Frontiers in Pharmacology, 2015, 6, article 262 (Year: 2015).*
Inoue et al "NLRP3 Inflammasome and MS/EAE" Autoimmune diseases, 2013, Article ID 859145, pp. 1-8 (Year: 2013).*
Inoue, Makoto et al., "Mechanism to Develop Inflammasome-Independent and Interferon-β-Resistant EAE with Neuronal Damages", Nature Neuroscience, Nov. 7, 2016, vol. 19, No. 12, pp. 1599-1609.
Khan, Nemat et al., "Pharmacological inhibition of the NLRP3 inflammasome as a potential target for multiple sclerosis induced central neuropathic pain", Inflammopharmacol, Sep. 30, 2017, vol. 26, Iss. 1, pp. 11-86.
Malhotra, Sunny et al., "NLRP3 inflammasome is associated with the response to IFNβin patients with multiple sclerosis", Brain, Jan. 12, 2015, vol. 138, pt. 3, pp. 644-652.
Marchetti, Carlo et al., "OLT1177, a β-sulfonyl nitrile compound, safe in humans, inhibits the NLRP3 Inflammasome and reverses the metabolic cost of inflammation", Proceedings of the National Academy of Sciences USA, Jan. 29, 2018, vol. 115, No. 7, pp. 1530-1539.
Skouras, Damaris, "Damaris Skouras—CEO of Olatec on Treating Inflammation", OneMedMarket News & Information Center, Dec. 23, 2016, pp. 1-4.
Toldo, Stefano et al., "Abstract 18066: Novel NLRP3 Inflammasome Inhibitor OLT1177 Reduces Infarct Size in a Mouse Model of Myocardial Ischemia Reperfusion Injury", Circulation, Nov. 14, 2017, vol. 136, Suppl. 1, p. 18066.
Youm, Yun-Hee et al., "Ketone Body β-Hydroxybutyrate Blocks the NLRP3 Inflammasome-Mediated Inflammatory Disease", Nature Medicine, Feb. 16, 2015, vol. 21, issue 3, p. 263-269.
International Search Report dated Mar. 12, 2018 issued in PCT/US2018/012455.

* cited by examiner

*Primary Examiner* — Yevgeny Valenrod
(74) *Attorney, Agent, or Firm* — Perkins Coie LLP; Viola T. Kung

(57) ABSTRACT

The present invention is directed to a method for treating multiple sclerosis by administering dapansutrile to a subject in need thereof. A preferred route of administration is oral administration.

9 Claims, 3 Drawing Sheets

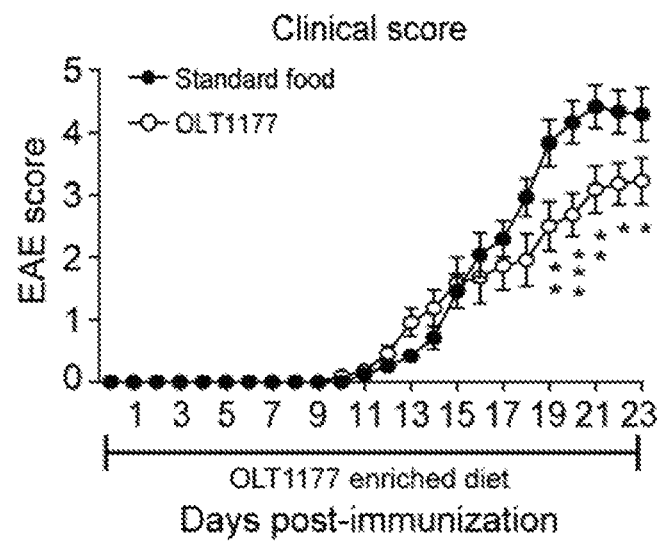
FIG. 2A
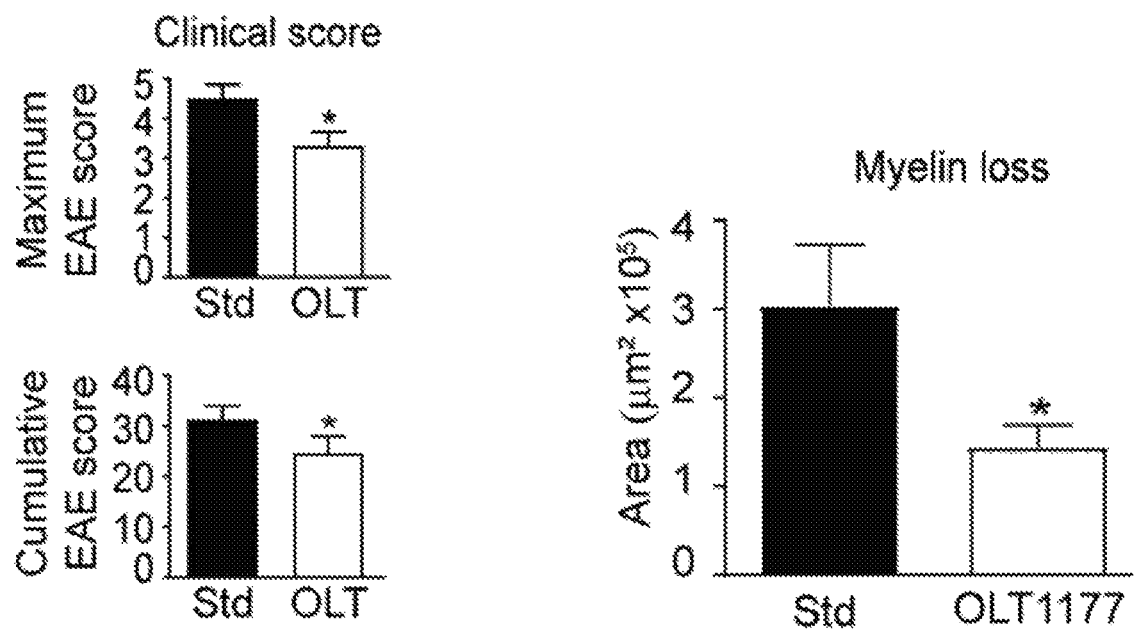
FIG. 2B
FIG. 2C

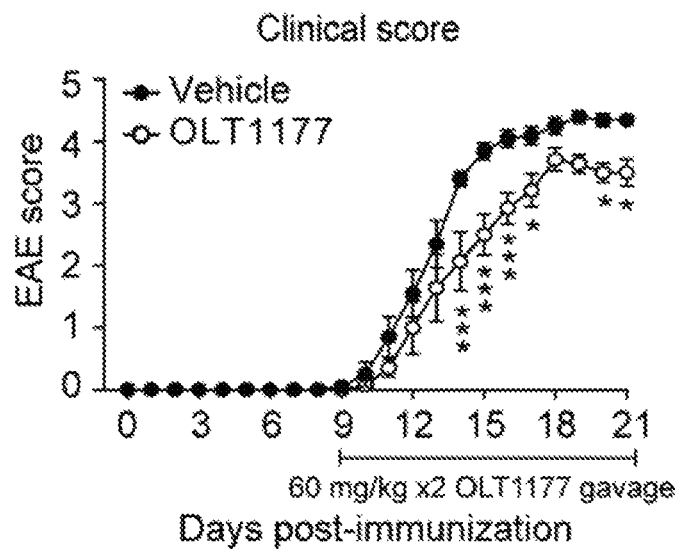
FIG. 3A
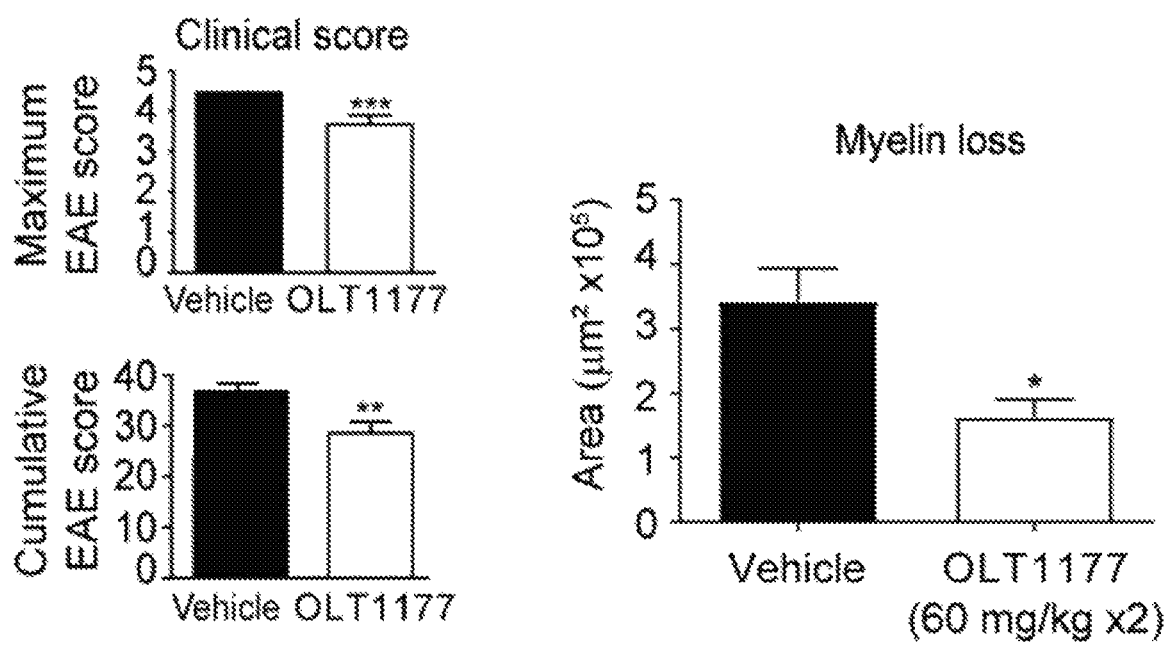
FIG. 3B
FIG. 3C

METHOD FOR TREATING MULTIPLE SCLEROSIS

This application is a continuation-in-part of PCT/US2018/012455, filed Jan. 5, 2018, which claims priority to U.S. Provisional No. 62/443,171, filed Jan. 6, 2017. The above applications are incorporated herein by reference in their entirety.

FIELD OF THE INVENTION

The present invention relates to a method for treating multiple sclerosis using a pharmaceutical composition comprising dapansutrile.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of Dec. 29, 2017, and a size of 533 bytes. The Sequence Listing filed via EFS-Web is part of the specification and is hereby incorporated in its entirety by reference herein.

BACKGROUND OF THE INVENTION

Multiple sclerosis (MS) is an autoimmune disease with the autoimmune activity directed against central nervous system (CNS) antigens. MS is an inflammatory demyelinating disease of the CNS, which results in damage to the protective covering (myelin sheath) that surrounds nerve fibers in the brain and spinal cord, leading to the loss of the myelin sheathing around neuronal axons (demyelination), axonal loss, and the eventual death of neurons, oligodendrocytes and glial cells.

When the myelin sheath is damaged, nerve impulses slow or even stop, causing neurological problems. MS is characterized clinically by relapses and remissions, often leading to progressive physical impairment. The cause of MS is unknown; however, pathologic, genetic, and immunologic features have been identified which suggest that the disease has an autoimmune basis. Although the antigenic target in MS is believed to be confined within the CNS, a systemic immunoregulatory defect may be present. T cells that were reactive to myelin basic protein (MBP) were detected in the blood of MS patients. Circulating blood cells of MS patients were also primed for enhanced cytokine synthesis. Exaggerated mitogen-inducible cytokine synthesis by peripheral monocytes was measured during the weeks immediately preceding the onset of episodes of relapsing MS. Thus, the exaggerated production of tumor necrosis factor (TNF), interleukin-1 (IL-1), and interferon-γ by circulating blood cells may serve as a peripheral trigger or marker for the induction of demyelinating inflammation in the CNS.

An estimated 2,500,000 people in the world suffer from MS. It is one of the most common diseases of the CNS in young adults. MS is a chronic, progressing, disabling disease, which generally strikes its victims sometime after adolescence, with diagnosis generally made between 20 and 40 years of age, although onset may occur earlier. The disease is not directly hereditary, although genetic susceptibility plays a part in its development. MS is a complex disease with heterogeneous clinical, pathological and immunological phenotype.

There are currently some available therapies in the clinic for the treatment of MS. However, most of them show poor efficacy, especially, in individuals who suffer from progressive. Moreover, they also have several side-effects (Wagner and Goverman, 2015, F1000Research 4:517; Pérez-Cerdá et al., 2016, Mult Scler Demyelinating Disord 1:9).

BRIEF DESCRIPTION OF THE DRAWING

FIG. 1A shows the average EAE clinical score of mice treated twice-daily by intraperitoneal administration of 60 mg/kg dapansutrile from Day 0 (day of immunization) to Day 21. FIG. 1B is a graph showing the quantification of demyelination in the lumbar spinal cord of mice treated with dapansutrile. *$p<0.05$; $p<0.01$; *$p<0.001$ vs. Vehicle. Two-way RM ANOVA with Bonferroni's post hoc test in 1A (n=9 in vehicle and n=10 in dapansutrile); Unpaired t-test in 1B (n=9 in vehicle and n=10 in OLT1177). Data are shown as mean±sem.

FIGS. 2A-2C shows dapansutrile (OLT1177™)-enriched food enhances functional and histological outcomes in EAE mice. Mice were fed with a standard diet or a diet supplemented with 3.75 g of dapansutrile per kg of food from Day 0 (day of immunization) to Day 23. FIG. 2A shows the evolution of the EAE clinical scores at days post-immunization of mice fed with a standard diet or a dapansutrile diet. FIG. 2B shows the cumulative and maximum EAE scores of mice fed with a standard diet or a dapansutrile diet. FIG. 2C shows the quantification of demyelination in the lumbar spinal cord of mice fed with a standard diet or a dapansutrile diet at 23 days after immunization. *$p<0.05$; $p<0.01$; *$p<0.001$. Two-way RM ANOVA, Bonferroni's post hoc test in 2A (n=11 per group); One-way ANOVA, Bonferroni's post hoc test in 2B (n=11 per group) and 2C (n=8 for standard food and n=11 for dapansutrile). Data are shown as mean±sem.

FIGS. 3A-3C show oral administration of dapansutrile mediate therapeutic effects in EAE mice. Mice were treated with twice-daily oral gavage of dapansutrile (OLT1177™, 60 mg/kg) or vehicle (water) from disease onset. FIG. 3A shows the average EAE clinical score of mice treated with dapansutrile or saline vehicle. FIG. 3B shows the cumulative and maximum clinical EAE scores of mice treated with dapansutrile or saline vehicle. FIG. 3C shows the quantification of demyelinating in the spinal cord of vehicle- or dapansutrule-treated mice. *$p<0.05$; $p<0.01$; *$p<0.001$ vs. vehicle. Two-way RM ANOVA with Bonferroni's post hoc test in 3A, n=10 for vehicle and n=7 for dapansutrile). Unpaired t-test in 3B (n=10 for vehicle and n=7 for dapansutrile) and 3C (n=9 in vehicle and n=7 for dapansutrile). Data are shown as mean±sem.

DETAILED DESCRIPTION OF THE INVENTION

Definitions

Figure 1A:
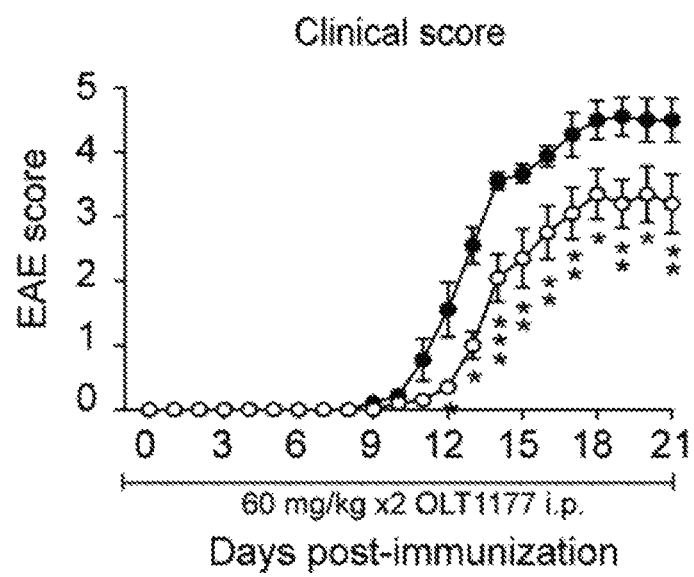
FIGS. 1A and 1B shows effects of prophylactic treatment of dapansutrile (OLT1177™) in experimental allergic encephalomyelitis (EAE) mice.

"About," as used herein, is ±10% of the recited value.

"An effective amount," as used herein, is the amount effective to treat a disease by ameliorating the pathological condition or reducing the symptoms of the disease.

"Pharmaceutically acceptable salts," as used herein, are salts that retain the desired biological activity of the parent compound and do not impart undesired toxicological effects. Pharmaceutically acceptable salt forms include various crystalline polymorphs as well as the amorphous form of the different salts. The pharmaceutically acceptable salts can be formed with metal or organic counterions and include, but are not limited to, alkali metal salts such as sodium or potassium; alkaline earth metal salts such as magnesium or calcium; and ammonium or tetraalkyl ammonium salts, i.e., $NX_4+$(wherein X is $C_{1-4}$).

"Pharmaceutically acceptable solvates," as used herein, are addition complexes in which the compound is combined with a Pharmaceuticallys acceptable co-solvent in some fixed proportion. Co-solvents include, but are not limited to, water, acetic acid, ethanol, and other appropriate organic solvents.

Description

The inventor has discovered that dapansutrile, or a pharmaceutically acceptable solvate thereof, is effective in treating multiple sclerosis. Dapansutrile (3-methanesulfonylpropionitrile), CAS#: 54863-37-5, has a formula weight of 133.17, and its structure is shown below.

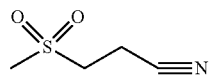

The present invention provides methods for preventing and/or treating a subject having multiple sclerosis and for preserving and/or increasing myelin content in a subject having multiple sclerosis. The method comprises administering an effective amount of dapansutrile to a subject suffering from multiple sclerosis.

There are four major clinical types of MS that the present invention is useful to treat: 1) relapsing-remitting MS, characterized by clearly defined relapses with full recovery or with sequelae and residual deficit upon recovery; periods between disease relapses characterized by a lack of disease progression; 2) secondary progressive MS, characterized by initial relapsing remitting course followed by progression with or without occasional relapses, minor remissions, and plateaus; 3) primary progressive MS, characterized by disease progression from onset with occasional plateaus and temporary minor improvements allowed; and 4) progressive relapsing MS, characterized by progressive disease onset, with clear acute relapses, with or without full recovery; periods between relapses characterized by continuing progression.

In one embodiment, dapansutrile prevents, slows down, or reduces neurodegeneration including demyelination and neuronal death.

The mouse experimental allergic encephalomyelitis (EAE) is an induced autoimmune demyelinating disease with many similarities to human MS in its clinical manifestations. The inventor has demonstrated that either oral or intraperitoneal dapansutrile treatment exerted protective effects on functional and histological outcomes in EAE mice when administered prophylactically. Further, therapeutic treatment after disease onset by dapansutrile resulted in protection against neurological decline and demyelination when administered orally.

Pharmaceutical Compositions

The active compound dapansutrile, or its pharmaceutically acceptable salt or solvate in pharmaceutical compositions in general is in an amount of about 0.1-5% for an injectable formulation, about 1-90% for a tablet formulation, about 1-100% for a capsule formulation, about 0.1-5% for a patch formulation, about 0.01-20%, or 0.05-20%, or 0.1-20%, or 0.2-15%, or 0.5-10%, or 1-5% (w/w) for a topical formulation.

Pharmaceutically acceptable carriers, which are inactive ingredients, can be selected by those skilled in the art using conventional criteria. Pharmaceutically acceptable carriers include, but are not limited to, non-aqueous based solutions, suspensions, emulsions, microemulsions, micellar solutions, gels, and ointments. The pharmaceutically acceptable carriers may also contain ingredients that include, but are not limited to, saline and aqueous electrolyte solutions; ionic and nonionic osmotic agents such as sodium chloride, potassium chloride, glycerol, and dextrose; pH adjusters and buffers such as salts of hydroxide, phosphate, citrate, acetate, borate; and trolamine; antioxidants such as salts, acids and/or bases of bisulfite, sulfite, metabisulfite, thiosulfite, ascorbic acid, acetyl cysteine, cystein, glutathione, butylated hydroxyanisole, butylated hydroxytoluene, tocopherols, and ascorbyl palmitate; surfactants such as lecithin, phospholipids, including but not limited to phosphatidylcholine, phosphatidylethanolamine and phosphatidyl inositiol; poloxamers and ploxamines, polysorbates such as polysorbate 80, polysorbate 60, and polysorbate 20, polyethers such as polyethylene glycols and polypropylene glycols; polyvinyls such as polyvinyl alcohol and povidone; cellulose derivatives such as methylcellulose, hydroxypropyl cellulose, hydroxyethyl cellulose, carboxymethyl cellulose and hydroxypropyl methylcellulose and their salts; petroleum derivatives such as mineral oil and white petrolatum; fats such as lanolin, peanut oil, palm oil, soybean oil; mono-, di-, and triglycerides; polymers of acrylic acid such as carboxypolymethylene gel, and hydrophobically modified cross-linked acrylate copolymer; polysaccharides such as dextrans and glycosaminoglycans such as sodium hyaluronate. Such pharmaceutically acceptable carriers may be preserved against bacterial contamination using well-known preservatives, these include, but are not limited to, benzalkonium chloride, ethylene diamine tetra-acetic acid and its salts, benzethonium chloride, chlorhexidine, chlorobutanol, methylparaben, thimerosal, and phenylethyl alcohol, or may be formulated as a non-preserved formulation for either single or multiple use.

For example, a tablet formulation or a capsule formulation of dapansutrile may contain other excipients that have no bioactivity and no reaction with the active compound. Excipients of a tablet may include fillers, binders, lubricants and glidants, disintegrators, wetting agents, and release rate modifiers. Binders promote the adhesion of particles of the formulation and are important for a tablet formulation. Examples of binders include, but are not limited to, carboxymethylcellulose, cellulose, ethylcellulose, hydroxypropylmethylcellulose, methylcellulose, karaya gum, starch, starch, and tragacanth gum, poly(acrylic acid), and polyvinylpyrrolidone.

For example, a patch formulation of dapansutrile may comprise some inactive ingredients such as 1,3-butylene glycol, dihydroxyaluminum aminoacetate, disodium edetate, D-sorbitol, gelatin, kaolin, methylparaben, polysorbate 80, povidone, propylene glycol, propylparaben, sodium carboxymethylcellulose, sodium polyacrylate, tartaric acid, titanium dioxide, and purified water. A patch formulation may also contain skin permeability enhancer such as lactate esters (e.g., lauryl lactate) or diethylene glycol monoethylether.

Topical formulations including dapansutrile can be in a form of gel, cream, lotion, liquid, emulsion, ointment, spray, solution, and suspension. The inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent). In one embodiment, diethylene glycol monoethylether is included in the topical gel formulation.

Method of Use

The present invention is directed to a method of preventing or treating multiple sclerosis. Dapansutrile, or the pharmaceutically acceptable salts thereof, can be used as is, or it can be administered in the form of a pharmaceutical composition that additionally contains a pharmaceutically acceptable carrier. The method comprises the steps of first identifying a subject in need thereof, and administering to the subject the active compound, in an amount effective to treat multiple sclerosis.

In one embodiment, the present method is effective in prophylactic treatment, which is a process of protecting against the development of MS by a treatment of dapansutrile before the onset of MS to affect pathogenesis. By prophylactic treatment, dapansutrile is administered to a patient in need thereof, before the onset of MS.

In another embodiment, the present method is effective in therapeutic treatment after the onset of MS, when the patient starts to show clinical signs. The dapansutrile treatment results in protection against neurological decline and demyelination.

In one embodiment, the subject has multiple sclerosis, such as relapsing-remitting multiple sclerosis, and is administered an effective amount of dapansutrile for a period of time sufficient to achieve one or more of the following changes: (a) reduced frequency of relapse in the subject, (b) reduced probability of relapse in the subject, (c) reduced annualized relapse rate in the subject, (d) reduced risk of disability progression in the subject, (e) reduced number of new or newly enlarging T2 lesions in the subject, (f) reduced number of new non-enhancing T1 hypointense lesions in the subject, and (g) reduced number of gadolinium (Gd+) lesions in the subject, wherein the changes (a)-(g) are relative to a subject treated with placebo, or the subject prior to treatment.

In another embodiment, a subject having relapsing-remitting multiple sclerosis is administered an effective amount of dapansutrile for a period of time sufficient to achieve one or more of the following changes: (a) reduced annualized relapse rate of at least 30%; (b) reduced risk of disability progression of at least 30%; and (c) reduced number of new or newly enlarging T2 lesions of at least 65% in the subject, wherein the changes (a)-(c) are relative to a subject treated with placebo, or the subject prior to treatment.

The pharmaceutical composition of the present invention can be applied by local administration or systemic administration. Local administration includes topical administration. Systemic administration includes oral, parenteral (such as intravenous, intramuscular, subcutaneous or rectal), and other systemic routes of administration. In systemic administration, the active compound first reaches plasma and then distributes into target tissues. Oral administration is a preferred route of administration for the present invention.

Dosing of the composition can vary based on the extent of the injury and each patient's individual response, and the possibility of co-usage with other therapeutic treatments including use of other therapeutic agents. For systemic administration, plasma concentrations of the active compound delivered can vary; but are generally $1 \times 10^{-10}$-$1 \times 10^{-4}$ moles/liter, and preferably $1 \times 10^{-8}$-$1 \times 10^{-5}$ moles/liter.

In one embodiment, the pharmaceutical composition is administrated orally to a subject. The dosage for oral administration is generally 0.1-100, 0.1-20, or 1-50 mg/kg/day, depending on the subject's age and condition. For example, the dosage for oral administration is 0.1-10, 0.5-10, 1-10, 1-5, or 5-50 mg/kg/day for a human subject. In one embodiment, the active compound can be applied orally to a human subject at 1-100, 10-50, 20-1000, 20-500, 100-800, or 200-600 mg/dosage, 1-4 times a day, depends on the patient's age and condition.

In one embodiment, the pharmaceutical composition is administrated intravenously to a subject. The dosage for intravenous bolus injection or intravenous infusion is generally 0.1-10, 0.03 to 5, or 0.03 to 1 mg/kg/day.

In one embodiment, the pharmaceutical composition is administrated subcutaneously to the subject. The dosage for subcutaneous administration is generally 0.1-1, 0.3-20, 0.3-3, or 1-6 mg/kg/day.

In one embodiment, the composition is applied topically. The composition is topically applied at least 1 or 2 times a day, or 3 to 4 times per day, depending on the medical issue and the disease pathology. In general, the topical composition comprises about 0.01-20%, or 0.05-20%, or 0.1-20%, or 0.2-15%, 0.5-10, or 1-5% (w/w) of the active compound. Typically 0.2-10 mL of the topical composition is applied to the individual per dose.

The time period for which the subject is dosed with the dapansutrile in any of the methods described above can range, for example, every day, every 2-4 days, or every week, from about 1 week to the remaining lifespan of the subject. Dapansutrile can be dosed, for example, for at least 1, 2, 3, 4, 5, 6, 7, 8, 9, 10, 20, 30, 40, or 50 weeks, or for at least 1, 2, 3, 4, 5, 6, 7, 8, 9, 10, 20, 30, 40, or 50 years.

Those of skill in the art will recognize that a wide variety of delivery mechanisms are also suitable for the present invention.

The present invention is useful in treating a mammal subject, such as humans, horses, and dogs. The present invention is particularly useful in treating humans.

The following examples further illustrate the present invention. These examples are intended merely to be illustrative of the present invention and are not to be construed as being limiting.

EXAMPLES

Example 1. Rat Model for Treating Multiple Sclerosis (Prophetic Example)

The experiments are performed according to Marin et al (Experimental Neurology, 131: 221-228 (1995)) with some modification; Marin et al is incorporated herein by reference.

The mouse experimental allergic encephalomyelitis (EAE) is an induced autoimmune demyelinating disease with many similarities to human MS in its clinical manifestations. In both EAE and MS, clinical disease is associated with blood-brain barrier dysfunction, infiltration of central nervous system by mononuclear cells (mainly macrophages and T lymphocytes, and serum products), and demyelination (Baker et al. J. Neuroimmunol., 1990, 28:261; Butter et al., J. Neurol. Sci., 1991, 104:9; Harris et al., Ann. Neurol., 1991, 29:548; Kermonde et al., Brain, 1990, 113:1477). The ability of dapansutrile to slow or prevent neurodegeneration including demyelination and neuronal death can be assessed in an EAE model.

Experimental Allergic Encephalomyelitis (EAE) Induction.

Rats are anesthetized with 2% isoflurane+02 and immunized on Day 0 in the footpad of the left hind limb with 0.1 ml of an emulsion containing myelin basic protein (MBP) at one of the following doses: 0, 1, 3, 10 or 30 μg (fragment 68-84). The MBP is dissolved in phosphate-buffered saline (PBS) and emulsified with an equal volume of complete Freund's adjuvant (CFA) containing 5 mg/ml of *Mycobacterium tuberculosis* H37Ra. Control rats receive 0.1 ml of the PBS/CFA emulsion with no MBP in the footpad of the left hind limb.

Clinical Scoring of EAE.

Evaluation of clinical disease is performed on a daily basis using a standard 0-5 scoring system. The spectrum of rating is 0, normal; 0.5, partial loss of tail tone; 1, complete loss of tail tone; 2, dragging of one hind limb; 3, paralysis of both hind limbs; 4, moribund; and 5, death. Daily weights are recorded for individual rats and weight loss/gain is expressed relative to initial weight.

Treatment of EAE.

Dapansutrile is diluted in about 200 μL of an oral vehicle such as Ora-Plus® and is given orally to rats at 1-500 or 10-100 mg/kg/day. Treatment with active compound begins at Day 0 or Day 9 after immunization with MBP and continued until 21 days post-immunization. The efficacy of four different dosing regimens is compared over that time period. In each experiment, the control rats received the same amounts of vehicle as the active compound-treated groups. Cyclosporin A is used as a positive control in some studies. Cyclosporin A (4 mg/kg) or vehicle (PBS) is administered subcutaneously on alternate days for 22 days beginning at the day of immunization.

CNS Pathology.

In a separate study, the effects of treatment with the active compound is determined on CNS pathology induced by immunization with MBP (0, 10, or 30 μg). Dapansutrile at 1-100 or 10-100 mg/kg/day is administered every other day beginning on Day 9 post-MBP. Animals are killed (via $CO_2$) on Days 9, 14, or 20 post-MBP injection. The brain and spinal cord from each rat are removed and placed in 10% neutral-buffered formalin. Following fixation for at least 72 h, cross sections of the brain are made at the optic chiasm caudal to the attachment of the pituitary and at the transverse fibers of the pons. The spinal cord is examined by making 4 to 6 cross sections through the cervical, thoracic, lumbar, and sacral portions. The sacral segment with attached caudal nerves is embedded longitudinally. Tissues are processed for paraffin embedding and stained with hematoxylin and eosin.

Histologic evaluations are performed without knowledge of the treatment groups. Each slide is assigned a numerical score ranging from 1 to 4 to indicate the intensity of inflammation and demyelination. Scoring criteria are as follows: 1, minimal with small perivascular cuffs of inflammatory cells surrounding one to two vessels; 2, mild with small perivascular cuffs of inflammatory cells surrounding three or more vessels with little if any extension of inflammation into parenchyma; 3, moderate with prominent perivascular cuffs of inflammatory cells with three or more vessels and moderate extension of the inflammation into the surrounding parenchyma; and 4, marked with the majority of vessels with prominent perivascular cuffs of inflammatory cells with extensive involvement of the neuropil in the inflammatory process.

A composite inflammatory score is determined for each rat for each CNS region. Means±SEM score values are computed for each portion of the CNS for each time point and compared against the vehicle-treated animals.

Statistical Analyses.

Values of clinical and histopathologic scoring are expressed as means±SEM. The integrated clinical score for each rat over the entire course of the disease is calculated as the area under the curve of daily clinical score versus time (units arbitrary). The values of the treated groups for integrated clinical scoring are compared statistically against those of the control group using the Mann-Whitney test. Student's t test is used to ascertain whether disease duration is reduced by the active compound.

Example 2. Prophylactic Treatment of Dapansutrile in EAE Mice by Intraperitoneal Administration EAE Induction Active immunization was done in female adult (8 weeks old) C57Bl/6 mice. Briefly, mice were subcutaneously injected with 300m of myelin oligodendrocyte glycoprotein (MOG)35-55 peptide (MEVGWYRSPFSRVVHLYRNGK, SEQ ID NO: 1) emulsified in complete Freund's Adjuvant (Sigma Aldrich) supplemented with 4 mg of micobacterioum tuberculosis H37RA (DIFCO Laboratories). On day 0 and 2 post-immunization, mice were also injected intraperitoneally (i.p.) with 500 ng of pertussis toxin (List Biological Laboratories).

Intraperitoneal Administration

Starting on day 0 (day of immunization), mice were injected intraperitoneally twice daily with dapansutrile (OLT1177™, 60 mg/kg) or saline until the end of the study (Day 21). Each treated group had 10 mice.

Functional Assessment

Animals were monitored daily for signs of EAE and the scoring system is as follows: 0=no clinical symptoms, normal walking; 0.5=partial paralyzed tail, 1=fully paralyzed tail; 2=mild hind-limb weakness, quick righting reflex; 3=severe hind-limb weakness, slow righting reflex, unable to bear weight; 3.5=severe hind-limb weakness and partial paralysis of hind limb; 4=complete paralysis of at least one hind limbs; 4.5=complete paralysis of one or both one hind limbs and trunk weakness; 5=complete paralysis of one or both hind limbs, forelimb weakness or paralysis; 6=mouse is found dead by EAE.

Histological Analysis

EAE mice were euthanized at either day 21 or 23 post-immunization with an overdose of pentobarbital sodium (Doletha1) and transcardially perfused with 4% paraformaldehyde (PFA) in 0.1M phosphate buffer (PB). Lumbar segments of spinal cords were harvested, post-fixed in 4% PFA for 2 hours and cryoprotected in 30% sucrose in 0.1M at 4° C. for at least 48 hours. Spinal cords were embedded in TissueTek OCT (Sakura), cut in transversal sections (15 μm-thick) with a cryostat (Leica) between L3 and L5 segments and serially picked up on gelatine-coated glass slides. Samples were stored at −20° C.

Sections were stained with Luxol Fast Blue (LFB) (Sigma Aldrich). Briefly, after a graded dehydration, sections were placed in 1 mg/mL of LFB solution in 96% EtOH and 0.05% acetic acid overnight at 37° C. and protected from light. Then, slides were washed with 96% EtOH, rehydrated in distilled water and placed in a 0.5 mg/mL $Li_2CO_3$ solution for 3-5 minutes at room temperature. Finally, sections were washed in distilled water, dehydrated again in 100% EtOH and mounted in DPX (Sigma Aldrich). To assess the demyelinated area in the spinal cord, 6 random images per mice were captured at 10× magnification with an Olympus BX51 and the attached Olympus DP73 Camera. The total demyelinated area within the spinal cord was measured with Image J image analysis software.

Results

Figure 1B:
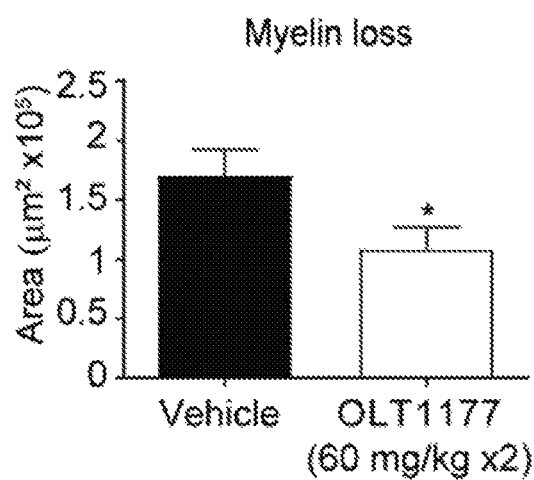

The onset of clinical signs of EAE was observed between day 9 and 12 post-immunization in mice injected with saline. From this time point, mice underwent progressive functional disabilities, reaching a plateau of maximal disease outcomes by day 18-19 post-immunization (FIG. 1A). Mice treated with dapansutrile displayed significant lower disease scores. Statistical analysis revealed significant differences in clinical score starting at day 11 post-immunization and remaining significantly reduced until the end of the study at day 21 (FIG. 1A). The results show that in an animal model of multiple sclerosis, dapansutrile treated group ameliorated clinical signs of disease at days 11-21, and reduced the demyelination in the spinal cord (FIG. 1B), comparing with the saline-treated group.

Example 3. Prophylactic Treatment of Dapansutrile in EAE Mice by Oral Administration EAE induction, functional assessment, and histological analysis were the same as those described in Example 2.

Starting on day 0 (day of immunization), EAE-mice were fed either a dapansutrile-enriched diet or a standard diet. The compositions of the food were identical, except that dapansutrile-enriched diet contained 3.75 g dapansutrile per kilogram of food, which is about 50 mg dapansutrile/kg animal weight/day based on food consumption of 4 g/day. Standard and dapansutrile-enriched food were prepared by Research Diets (New Brunswick, N.J., USA). Food and water were provided ad libitum for the entire length of the study 23 days post EAE induction.

The results are shown in FIGS. 2A-2C. Mice orally treated with dapansutrile ameliorated the neurological deficits of EAE disease, as shown having lower daily EAE clinical scores after disease onset (FIG. 2A), and lower maximum EAE scores and lower cumulative EAE scores (FIG. 2B), comparing with those of control mice.

Further, in line with functional outcomes, histological analysis revealed that spinal cords from mice fed the dapansutrile diet had about 2-fold reduced demyelination than mice receiving the standard food (FIG. 2C).

Example 4. Oral Treatment with Dapansutrile in EAE Mice Starting at Disease Onset EAE induction, functional assessment, and histological analysis were the same as those described in Example 2.

60 mg/kg of dapansutrile was solubilized with distilled water and administered daily by oral gavage at 60 mg/kg animal weight to mice twice per day. Treatment was initiated on the first day the animals displayed the first signs of EAE until the end of the follow up. Control mice were administered distilled water at the same days. In this experiment, dapansutrile was administered by gavage and not directly in the diet because EAE mice show reduced food intake as a consequence of the disease.

The results are shown in FIGS. 3A-3C. Mice treated with dapansutrile showed reduced neurological deficits despite treatment was initiated at disease onset. Indeed, mice treated with dapansutrile showed a reduction about 1 point in the EAE score compared to mice given with vehicle (FIG. 3A). Dapansutrile also significantly reduced the cumulative and maximum clinical scores in EAE (FIG. 3B). Furthermore, dapansutrile provided a protection against demyelination as revealed the histological analysis of LFB stained spinal cords (FIG. 3C). These data support the beneficial effects of the therapeutic administration of dapansutrile to treat multiple sclerosis.

Example 5. Treating Multiple Sclerosis in Humans (Prophetic Example)

A study is conducted to evaluate the efficacy and safety of dapansutrile over 2 years in human subjects with relapsing-remitting multiple sclerosis ("RR-MS").

Subjects 18-55 years of age with McDonald criteria diagnosis of RR-MS and an Expanded Disability Status Scale score of 0.0-5.0 (EDSS, see Definition in US2014/0163100, which is incorporated herein by reference) are eligible for enrolment. Subjects are randomly assigned in a 1:1:1 ratio to placebo, dapansutrile PO twice daily (BID), or dapansutrile three times daily (TID), in an amount of 10-300 mg per dosage. Safety and tolerability are assessed by continuous adverse event monitoring and laboratory tests at all monthly visits. Additionally, physical examination, vital signs, and 12-lead ECG are evaluated.

The primary endpoint of the study is the proportion of subjects relapsing at 2 years, with relapses confirmed by an independent neurology evaluation committee to ensure consistent and accurate reporting across sites. Secondary clinical efficacy endpoints at 2 years are the annualized relapse rate (ARR) and disability progression using EDSS.

It is to be understood that the foregoing describes preferred embodiments of the present invention and that modifications may be made therein without departing from the scope of the present invention as set forth in the claims.

What is claimed is:

1. A method for treating multiple sclerosis, comprising the step of administering to a subject in need thereof an effective amount of dapansutrile.

2. The method according to claim 1, wherein said compound is administered by systemic administration.

3. The method according to claim 1, wherein said compound is administered by oral administration.

4. The method according to claim 1, wherein said treatment is prophylactic treatment before the onset of multiple sclerosis.

5. The method according to claim 1, wherein said treatment is therapeutic treatment after the onset of multiple sclerosis.

6. The method according to claim 1, wherein said multiple sclerosis is relapsing-remitting multiple sclerosis, secondary progressive multiple sclerosis, primary progressive multiple sclerosis, or progressive relapsing multiple sclerosis.

7. The method according to claim 6, wherein said multiple sclerosis is relapsing-remitting multiple sclerosis.

8. The method according to claim 7, wherein dapansutrile is administered for a period of time sufficient to achieve one or more of changes selected from the group consisting of: (a) reduced frequency of relapse in the subject, (b) reduced probability of relapse in the subject, (c) reduced annualized relapse rate in the subject, (d) reduced risk of disability progression in the subject, (e) reduced number of new or newly enlarging T2 lesions in the subject, (f) reduced number of new non-enhancing T1 hypointense lesions in the subject, and (g) reduced number of gadolinium (Gd+) lesions in the subject.

9. The method according to claim 7, wherein dapansutrile is administered for a period of time sufficient to achieve one or more of changes selected from the group consisting of: (a) reduced annualized relapse rate of at least 30%; (b) reduced risk of disability progression of at least 30%; and (c) reduced number of new or newly enlarging T2 lesions of at least 65% in the subject.

* * * * *